United States Patent [19]

Martin

[11] Patent Number: 4,722,732

[45] Date of Patent: Feb. 2, 1988

[54] INTRAVENOUS FLUID SUPPLY SYSTEM

[76] Inventor: James Martin, 8322 County Line Rd., Burr Ridge, Ill. 60521

[21] Appl. No.: 920,468

[22] Filed: Oct. 20, 1986

[51] Int. Cl.$^4$ .............................................. A61M 5/00
[52] U.S. Cl. .................................... 604/132; 604/248; 604/251
[58] Field of Search .................................. 604/82–86, 604/246–262, 132, 141

[56] References Cited

U.S. PATENT DOCUMENTS

| | | | |
|---|---|---|---|
| 1,664,938 | 4/1928 | McDonnell | 604/251 X |
| 2,129,983 | 9/1938 | Bacon | 604/251 |
| 3,468,308 | 9/1969 | Bierman | 604/141 |
| 3,506,005 | 4/1970 | Gilio et al. | 604/132 |
| 3,690,318 | 9/1972 | Gorsuch | 604/246 X |
| 4,143,659 | 3/1979 | Biedermann | 604/251 |
| 4,545,783 | 10/1985 | Vaughan | 604/251 |
| 4,588,396 | 5/1986 | Stroebel et al. | 604/246 |

Primary Examiner—Dalton L. Truluck
Attorney, Agent, or Firm—Edmond T. Patnaude

[57] ABSTRACT

An intravenous fluid system incorporates an elastomeric reservoir in which the intravenous fluid is retained under pressure and fed at a controlled rate to a cannula which is inserted into the patient. The reservoir is contained in a translucent housing which is open to the atmosphere through a check valve and which is connected to the line connecting the reservoir to the cannula through another check valve which permits flow of fluid into the housing when the outlet of the cannula is plugged.

13 Claims, 3 Drawing Figures

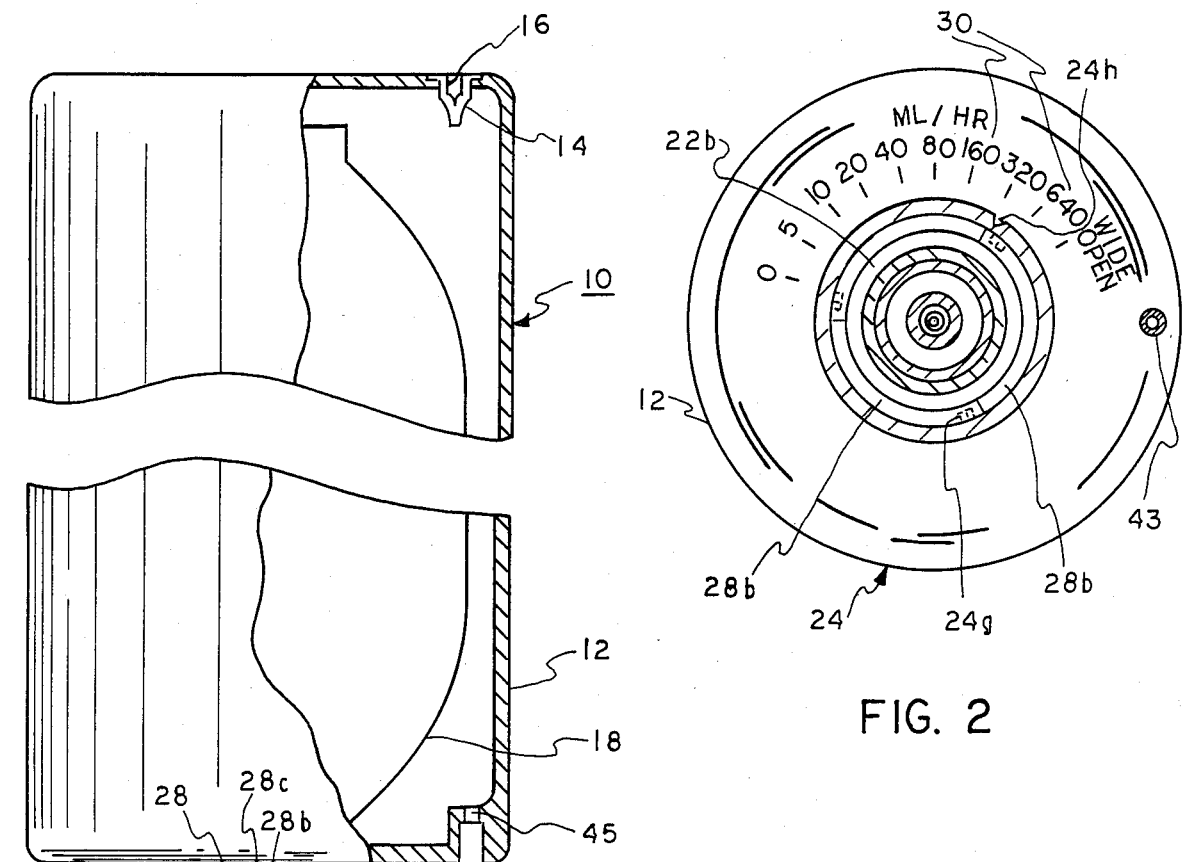
FIG. 2
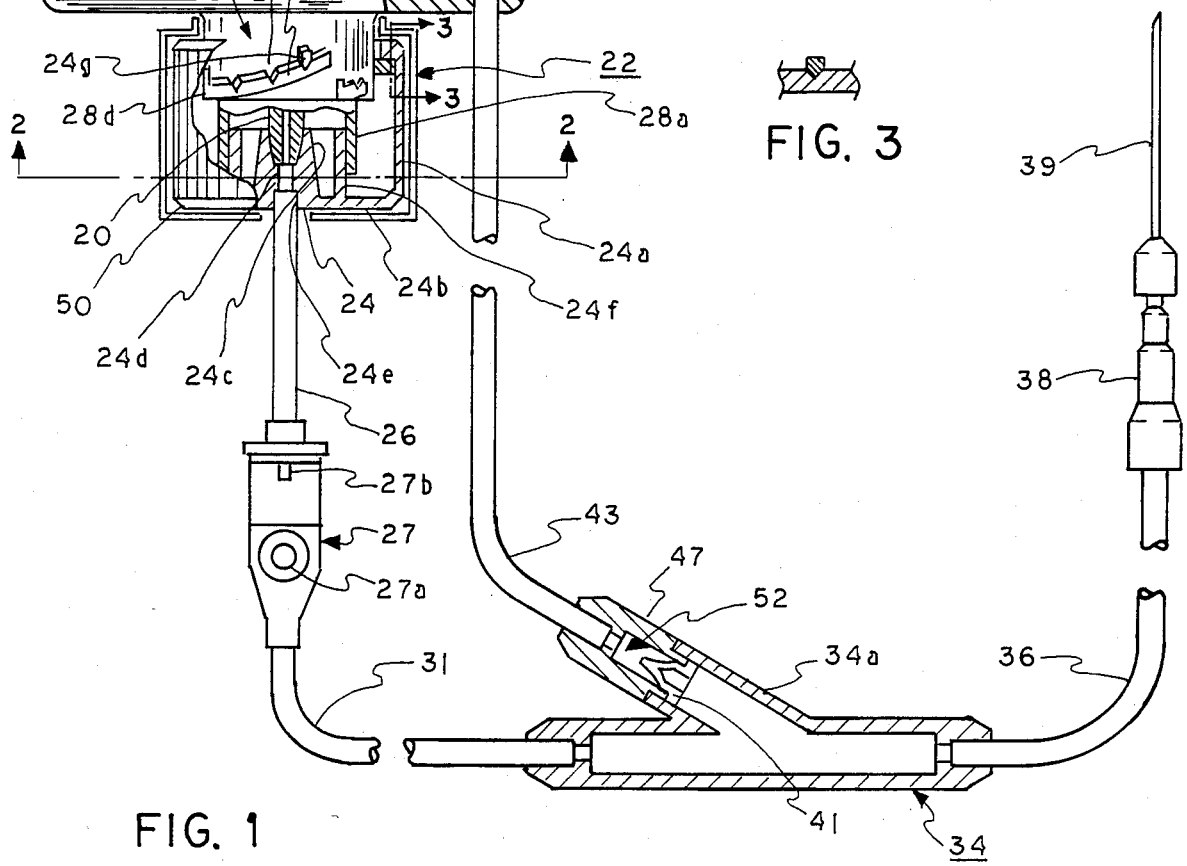
FIG. 3
FIG. 1

INTRAVENOUS FLUID SUPPLY SYSTEM

The present invention relates in general to systems for supplying intravenous fluids to a patient, and it relates in particular to a new and improved system which incorporates an elastomeric reservoir in which the intravenous fluid is maintained under a substantially constant pressure during the supply of the fluid to the patient.

BACKGROUND OF THE INVENTION

I.V. systems have generally been of two basic types, one, a gravity feed system in which a collapsible fluid reservoir located in an elevated position is connected to the patient through a manually adjustable valve, and two, a system in which the fluid is physically pumped at an adjustable rate of flow and pressure to the patient. In the first system the feed pressure is limited, while the second system is relatively complex and expensive to manufacture and to maintain. While the use of a pump enables the feeding of fluids under high pressure to the arteries of a patient the pump must be powered by electricity which has restricted its use.

SUMMARY OF THE INVENTION

Briefly, there is provided in accordance with the present invention a new and improved system for supplying intravenous fluids to a patient wherein the fluid is retained under pressure in an elastomeric reservoir and supplied to the patient through a manually adjustable metering valve. In a preferred embodiment of the invention the reservoir is housed in a partially translucent housing which is open to the atmosphere through an air inlet located near the top. A flexible feed tube connects the outlet of the metering valve to a cannula for feeding the fluid to the veins or arteries of the patient and a fluid return line, which includes a check valve, is connected between a fluid inlet in the housing and a location in the flexible feed tube between the cannula and the metering valve. In the event that the cannula is misplaced in the patient, the intravenous fluid flows through the return line to the housing where it is collected and provides a visible indication through the translucent portion thereof that the fluid is not flowing to the patient.

In accordance with another feature of the invention, a transparent drip chamber is provided with a self-sealing wall through which air may be injected into the drip chamber.

GENERAL DESCRIPTION OF THE DRAWINGS

Further objects and advantages and a better understanding of the present invention will be had by reference to the following detailed description taken in connection with the accompanying drawing wherein:

FIG. 1 is a partially cross-sectioned view of a pressurized intravenous fluid injection system embodying the present invention;

FIG. 2 is a cross-sectional view taken along the line 2—2 of FIG. 1; and

FIG. 3 is a cross-sectional view taken along the line 3—3 of FIG. 1.

DETAILED DESCRIPTION OF A PREFERRED EMBODIMENT

A complete system for feeding intravenous fluids under pressure to a patient is identified by the reference character 10 and includes a generally cylindrical housing 12 formed of a liquid impervious material such as plastic and which is connected to the atmosphere by means of a uni-directional check valve 14 which is mounted over an air inlet opening 16 at the top of the housing to permit air to enter the housing while preventing the flow of fluid out of the housing through the valve 14. Mounted within the housing 12 is an elastomeric reservoir 18 which contains the intravenous fluid to be administered to the patient. The reservoir 18 may be of the type described in U.S. Pat. No. 4,387,833 and thus includes an outer rubber sleeve and an inner flexible plastic bag which is formed of a material which is inert with respect to the intravenous fluid carried thereby. The fluid is initially fed under pressure into the reservoir 18 causing the rubber shell to expand and thereafter to exert pressure on the fluid contents. A spring loaded outlet valve (not entirely shown) is provided at the lower end of the reservoir 18 and includes a nozzle 20 which is biased in an outward direction by the valve spring. When the nozzle 20 is pressed toward the reservoir, the valve is opened to permit the intravenous fluid to flow out through the nozzle 20. As the nozzle is pressed farther towards the reservoir the aperture through the valve increases and therefore the rate of flow through the nozzle 20 also increases. Valves of this type are commonly used with fluid dispensers such, for example, as aerosol cans and the like and any suitable type may be used.

In order to permit manual adjustment of the rate of fluid flow from the nozzle 20 there is provided a metering adjustment mechanism 22 which includes a cup-like cap 24 having a cylindrical flange 24a and a bottom end 24b. An axial boss 24c sealably fits over the nozzle 20 and is provided with a central bore 24d which is aligned with the bore through the nozzle 20. A counterbore 24e is provided along the axis of the cap 24 and sealably receives the end of a flexible plastic feed tube 26. Connected to the other end of the feed tube 26 is an airtight drip chamber 27 which provides a visible indication of the rate at which the intravenous fluid is being infused to the patient.

The cap 24 further includes an internal cylindrical flange 24f which is rotatably received in a generally tubular base member 28. More particularly, the base member 28 is affixed to the bottom of the housing 12 over a centrally disposed outlet therein and includes a depending hollow cylindrical portion 28a into which the flange 24e partially and rotatably extends. The member 28 further includes three helical ramps 28b which are respectively provided with a plurality of spaced apart notches 28c on the upper edge thereof for respective cooperation with three lugs 24g provided on the inside surface of the flange 24a at locations spaced 120 degrees apart. Preferably the notches are V-shaped and the lower surface of the lugs 24g, as shown in FIG. 1, are also V-shaped to complement the shape of the notches. The ramps 28b are provided at the bottom edges thereof with upstanding stop shoulders 28d which are in engagement with the lugs 24g when the knob is positioned in its fully retracted position wherein the valve portion of the nozzle 20 is closed.

In order to controlably adjust the rate of flow of intravenous fluid through the tube 26 from the reservoir 18, the operator presses the cap 24 towards the housing and rotates it to that position wherein the lugs 24 are received in the notches which are located at that position. When the cap is released it will then remain in that set position. Inasmuch as the pressure within the reservoir 18 remains substantially constant until substantially all of the fluid has been exhausted from the reservoir the flow rate remains constant at the set value.

As best shown in FIG. 2 the cap 24 is provided with a V-shaped reference notch 24h which together with a plurality of graduation marks 30 on the bottom of the housing 12 provides a visual indication of the rate of flow of intravenous fluid from the reservoir 18.

It will be understood that any other suitable metering valve may be used to control the flow rate from the reservoir. A flexible plastic feed tube 31 is fitted at one end into the outlet port at the bottom of the drip chamber 27 and its other end is fitted into a Y-shaped fitting 34 having a main straight-through tubular section and a branch section 34a. Another flexible tube 36 is connected at one of its ends to the other end of the fitting 34, and the tube 36 is connected at its other end to a cannula 38 which includes a needle 39 which is adapted to be inserted through the skin of the patient into, for example, either a vein or an artery. A suitable clamp (not shown) may be located on the tube 36 for interrupting the flow of fluid to the patient. The branch leg or section of the fitting 34 identified by the reference character 34a may be seen to contain a check valve 41 for transmitting fluid in one direction only, away from the patient, to a flexible tube 43 which is connected at its upper end to a return inlet port 45 in the bottom of the housing 12. The leg 34a of the connector 34 includes a removable tubular end piece 47 which facilitates assembly of the check valve 41 within the leg 34a. The purpose of the return line which includes the check valve 41 is to return the I.V. fluid to the portion of the housing which is exterior of the reservoir 18 in the event that the needle 39 is misplaced in the patient and the I.V. fluid is not being fed either to a vein or an artery. When that occurs the fluid backs up in the cannula 38 and in tube 36 and thus flows to the housing through the return line.

The housing 12 is preferably formed of a translucent material but it may be opaque and include a translucent portion in the side wall near the bottom through which the fluid returned to the housing can be seen, thereby providing a visible indication to the operator that the needle 39 has been misplaced in the patient.

The check valve 41 provides an occlusion safety valve and is set to open at a differential pressure which is less than the back pressure which would occur in the tube 36 if the end of the needle 39 were blocked. This pressure is dependent upon whether the infusion is venous or arterial and to some extent on the blood pressure of the patient.

In order to prevent accidental opening of the valve during handling and shipping of the system, the cap 24 and the external portion of the base member 28 are covered with a plastic shrink safety seal 50 which must be removed before the cap 24 can be depressed to release the intravenous fluid from the reservoir 18. The safety seal also prevents tampering with the contents of the system.

In accordance with another feature of the present invention, means are provided in the return line from the fitting 34 for increasing the visibility of the fluid returned to the housing 12. In one embodiment of the invention as illustrated in FIG. 1, a small quantity of a dye 52 is inserted in the end fitting 47 in proximity to and downstream of the check valve 41 so that as the fluid passes through the check valve 41 its color is changed and made more visible as the dye 52 dissolves into the fluid. If desired, a narrow transverse passageway can be provided through the wall of the cap end fitting 47 so that as fluid passes therethrough air is educted through the passageway and appears as bubbles in the fluid as it passes through the tube 43. Ordinarily and preferably, all of the tubes 26, 36 and 43 are at least partially transparent so that the colored fluid passing through the tube 43 can be observed by the operator.

As indicated hereinabove, it is preferred that the entire housing 12 be translucent or transparent so that any of the intravenous fluid which is returned to the housing can be seen. In addition, the transparent or translucent housing permits observation of the reservoir 18 which decreases in size as the contents are depleted. In this way the operator can observe the reservoir 18 and thus estimate the amount of intravenous fluid remaining in the system.

In accordance with still another important aspect of the present invention the drip chamber, which is formed of a transparent rigid material such as glass or plastic, is provided in the wall thereof with an air injection port covered by a self sealing rubber or rubber-like disc member 27a. In normal use, the intravenous fluid enters the drip chamber through a capillary tube 27b known as a drip former and the fluid drips as discrete drops through the air pocket at the top of the chamber. The attendant can observe the flow rate through the wall of the drip chamber.

If the air escapes from the drip chamber, there is no way for the attendant to observe the flow rate of intravenous fluid into the patient, and since the reservoir 18 contains no air, in the absence of the injection port it would be very difficult and time consuming to re-establish the air bubble. However, the self-sealing member 27a permits the injection of air into the drip chamber by means of a hypodermic needle inserted into the chamber through the member 27a. When the needle is withdrawn, the opening through the member is automatically resealed. Materials from which the disc member may be formed are well known in the art, being used, for example, in the walls of I.V. bags for use in injecting medicaments and the like into the otherwise sealed bag.

Operation

In use, the system shown in FIG. 1 is supplied from the manufacturer as a unit with the reservoir 18 filled with a particular intravenous fluid and some means, such as a label on the housing, is provided to indicate the type of intravenous fluid contained therein. The entire system is maintained in a sterilized condition with the cannula 38 being enclosed in the normal manner during shipment and storage. When ready for use, the housing 12 can be placed in an upright position either above or below the patient, the shrink wrap 50 is then torn off and the cover 24 is pressed in and turned a small amount to fill the line 36 with the fluid. The operator having inserted the needle into the vein or artery of the patient then connects it to the line 36 and rotates the cover 24 to align the groove 24h with the graduation 30 on the bottom of the housing which indicates the desired flow rate. By observing the housing 12 the operator can then see if any of the fluid is being returned to the housing. If there is no return flow then the operator knows that the needle has been properly inserted into the patient and that the intravenous fluid will flow into the patient at the preset rate. If, on the other hand, the fluid is being returned to the housing, the operator knows that the needle should be repositioned.

It will be seen by those skilled in that art that the use of a self-pressurized intravenous fluid reservoir has many advantages over the heretofore used gravity feed system. Unlike the gravity feed systems where the flow rate is dependent on the height of the I.V. bag above the patient and thus varies appreciably when the patient rolls over, the flow rate in the pressurized system is relatively constant. Because higher pressures can be provided, direct infusions can be made into the arteries or other parts of the patient, such, for example, as into the bladder.

Also, in emergency situations as in accidents, it is unnecessary to find a place to hang the bag. For example, the drip chamber 27 can be taped to the side of the housing 12 which can then be placed in an upright position above or below the patient so that the flow rate can be observed in the chamber 27 as drops form and fall from the bottom of the drip tube 27b.

While the present invention has been described in connection with a particular embodiment thereof, it will be understood by those in the art that many changes may be made without departing from the true spirit and scope of the present invention. Therefore, it is intended by the appended claims to cover all such changes and modifications which come within the true spirit and scope of this invention.

What is claimed:

1. Apparatus for supplying an intravenous fluid to a patient, comprising in combination
   an elastomeric reservoir containing a quantity of intravenous fluid under pressure,
   an outlet port from said reservoir,
   cannula means for insertion into a vein or artery of said patient,
   a first conduit connected between said cannula and said outlet port for carrying said fluid to said cannula,
   metering valve means disposed between said port and said cannula for adjustably controlling the rate of flow of said fluid from said reservoir to said cannula,
   a housing,
   an air inlet port in said housing,
   a fluid return inlet port in said housing,
   a second conduit connected between said first conduit and said return inlet port, and
   first check valve means in said second conduit for preventing the flow of fluid therethrough toward said cannula.

2. Apparatus according to claim 1 comprising
   drip chamber means connected between said outlet port and said cannular for providing a visual indication of the rate of flow of said fluid to the patient.

3. Apparatus according to claim 2 wherein said drip chamber comprises
   a rigid transparent casing enclosing a drip chamber,
   a drip tube means opening into the top of said chamber,
   a self sealing injection port in said casing for receiving a hollow needle through which air may be injected into said chamber, and
   a fluid outlet port at the bottom of said casing.

4. Apparatus according to claim 2 comprising
   a rigid housing enclosing said reservoir,
   flexible tube means connecting said outlet port to said drip chamber means,
   said flexible tube means being sufficiently long to permit said drip chamber means to be positioned against the side of said housing.

5. Apparatus according to claim 2 comprising
   means exclusive of the intravenous fluid path through said drip chamber for injecting air into said chamber.

6. Apparatus for supplying an intravenous fluid to a patient, comprising in combination
   an elastomeric reservoir containing a quantity of intravenous fluid under pressure,
   an outlet port from said reservoir,
   metering valve means disposed over said port for adjustably controlling the rate of flow of said fluid from said reservoir,
   cannula means for insertion into a vein or artery of said patient,
   a first conduit connected between said cannula and said metering valve means for carrying said fluid to said cannula,
   an impervious housing enclosing said reservoir,
   an air inlet port in said housing,
   a fluid return inlet port in said housing,
   a second conduit connected between said first conduit and said return inlet port, and
   first check valve means in said second conduit for preventing the flow of fluid therethrough toward said cannula.

7. Apparatus according to claim 6, comprising
   second check valve means connected over said air inlet port for preventing the flow of fluid out of said housing through said air inlet port.

8. Apparatus according to claim 8, wherein
   said air inlet port is located at a substantial distance above said fluid return inlet port.

9. Apparatus according to claim 8 wherein
   said housing includes a translucent portion through which the level of return fluid in said housing can be observed.

10. Apparatus according to claim 8 comprising
    means disposed between said first check valve means and said housing for providing a visible indication of fluid flow in said second conduit.

11. Apparatus according to claim 6 comprising
    a tubular member mounted in said first conduit means,
    said tubular member having a branch conduit therein, and
    said first check valve means being mounted in said branch conduit.

12. Apparatus according to claim 12 wherein said first conduit means comprises
    a first flexible tube connected between said metering valve means and said tubular member, and
    a second flexible tube connected between said tubular member and said cannula.

13. Apparatus according to claim 12 wherein said second conduit means comprises
    a third flexible tube connected between said tubular member and said fluid return inlet port.

* * * * *